United States Patent [19]

Tanguy

[11] 3,955,066
[45] May 4, 1976

[54] TEMPERATURE REGULATION OF HEATING CYLINDER

[75] Inventor: Pierre Tanguy, Daix, France

[73] Assignee: Etud, Dijon, France

[22] Filed: June 7, 1974

[21] Appl. No.: 477,291

[30] Foreign Application Priority Data
June 13, 1973 France .............................. 73.21444
May 6, 1974 France .............................. 74.15503

[52] U.S. Cl. ............................... 219/471; 337/140; 337/395
[51] Int. Cl.² ........................................... H05B 1/02
[58] Field of Search ........... 219/469, 470, 471, 512; 337/140, 395; 236/9.6, 101 E, 101 R

[56] References Cited
UNITED STATES PATENTS 2,737,554   3/1956   Tiffany ............................. 337/395
3,737,826   6/1973   Simmons ........................... 337/395

*Primary Examiner*—J. D. Miller
*Assistant Examiner*—Fred E. Bell
*Attorney, Agent, or Firm*—Raymond A. Robic; Arthur Schwartz

[57] ABSTRACT

A thermostatic regulating device for the surface of a heating cylinder of a cooking appliance consisting essentially of a stretched metal wire applied along a spiral path with a wide helix angle to the surface of the cylinder, the variations in the length of the wire due to heat-induced expansion or contraction acting after amplification on a microswitch incorporated in the heating circuit for said cylinder.

18 Claims, 6 Drawing Figures

TEMPERATURE REGULATION OF HEATING CYLINDER

BACKGROUND OF THE INVENTION

This invention relates to the temperature regulation of heating cylinders installed in cooking appliances, including automatic pancake-making machines.

PRIOR ART

It is known that temperature regulation for heating cylinders of cooking appliances can be carried out either by introducing a thermostat of suitable form, namely an electrical-contact thermostat or the bulb of a gas-expansion thermostat, into a recess formed in the heating mass of the cylinder, or by arranging a contact thermostat on the inner surface of the cylinder, an opening being formed therein so as to provide access both for installation and for regulation.

Control means of this kind are attended by various disadvantages. In the case of thermostats accommodated in the mass of the cylinder, a sufficient thickness of the cylinder body must be available, which can make this type of regulation impossible for small machines. In the case of contact thermostats, they react as much as by conduction as by atmospheric contact which can interfere with regulation. Since in both cases the control of heat affects only a small local zone of the cylinder, excesses or deficits of heat can arise in other zones remote from the regulated zone.

OBJECT OF THE INVENTION

The object of the invention is to obviate these various disadvantages.

BRIEF SUMMARY OF THE INVENTION

According to the invention there is provided a thermostatic regulating device for the surface of a heating cylinder, comprising a metal wire applied to the surface of the cylinder under longitudinal tension and along a spiral path with a large helix angle, the variations in the length of this wire attributable to thermal expansion or contraction acting after amplification on a microswitch incorporated in the heating circuit of said cylinder.

FURTHER FEATURES OF THE INVENTION

According to another aspect of the invention, the wire of the thermostatic regulating device for the surface of the cooking cylinder is additionally used for removing pancakes in automatic pancake-making machines.

According to a further feature of the invention, the various components for placing the metal wire under tension, for breaking the heating circuit and for amplification are permanently assembled on a rigid base plate with means for centering and fixing them to the frame of the machine incorporating said heating surface.

DESCRIPTION OF EMBODIMENTS

Figure 1:
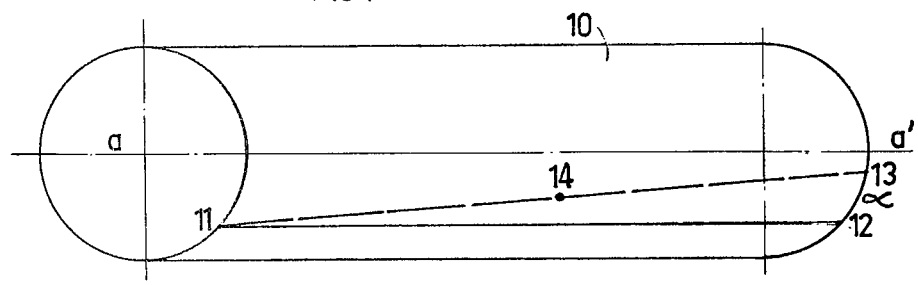
FIGS. 1 and 2 are diagrammatic perspective views of the regulating device.

In the cylinder 10 shown in FIG. 1, the reference 11 denotes a point of one of the base circumferences of the cylinder, whilst the reference 12 denotes the point of the other base circumference at the end of the generatrix starting from the point 11. The reference 13 denotes a first point separated from the point 12 by any angle $\alpha$ on the same circumference. The straight line 11–12 follows the surface of the cylinder, in other words the distance of any point of this straight line from the axis $aa'$ of the cylinder is constant and equal to the radius of the cylinder. The straight line 11–13 penetrates into the mass of the cylinder to a greater or lesser extent, depending upon the size of the angle $\alpha$, in other words the distance of any point of the straight line from the axis $aa'$ decreases from the point 11 to the medium point 14 and subsequently increases up to the point 13.

Figure 2:
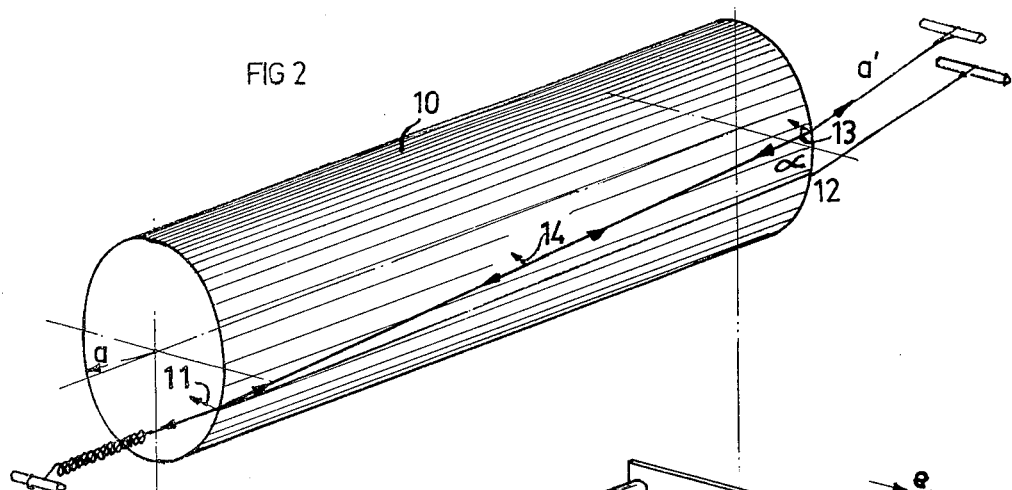

If the straight line 11–12 is in practice a metal wire, for example a steel wire, under longitudinal tension as shown in FIG. 2, i.e. with the tension inclined towards the axis $aa'$ of the cylinder so as to apply a pressure to the edges of the cylinder at 11 and 12 under the effect of the rigidity of the wire, the strand 11–12 will assume a very slightly curved form relative to the generatrix, which signifies that the pressure of a point of this strand against the cylinder decreases from the point 11 to the median point, subsequently increasing again to the point 12. If in practice the straight line 11–13 is itself a steel wire under longitudinal tension in the same way as the wire 11–12, part of this strand being pushed towards the outside of the cylinder to rest on its surface, the results is a reaction force which corresponds to an increase in the pressure of the points of this strand against the cylinder, this increase being at its greatest at the point 14. Accordingly, by suitably selecting the angle $\alpha$, it is possible to apply a stretched wire 11–13 whose contact pressure against the surface of the cylinder is substantially constant over the entire length of this strand. This angle is generally less than 20°.

Thus, a wire of this kind will give a true measure of the actual temperature of the cylinder not only along the helical strand 11–13, but also over the entire surface of the cylinder when it rotates about its axis against the wire.

We have previously proposed, in our U.S. application No. 241,309, for removing pancakes from the cooking cylinder, the use of a wire of stainless steel mounted and held under tension by a spring between two end rockers, the arrangement as a whole being pressed resiliently by a second spring against the surface of the cooking cylinder.

The wire in question, used for removing the pancakes once they had been cooked, was directed like the strand 11–12 along a generatrix of the cylinder. If this wire is now mounted in the same way as the strand 11–13, release of the pancakes will be improved in view of the fact that all the points of the wire will now come into contact with the surface of the cylinder under a substantially constant pressure over the entire length of the wire.

Figure 3:
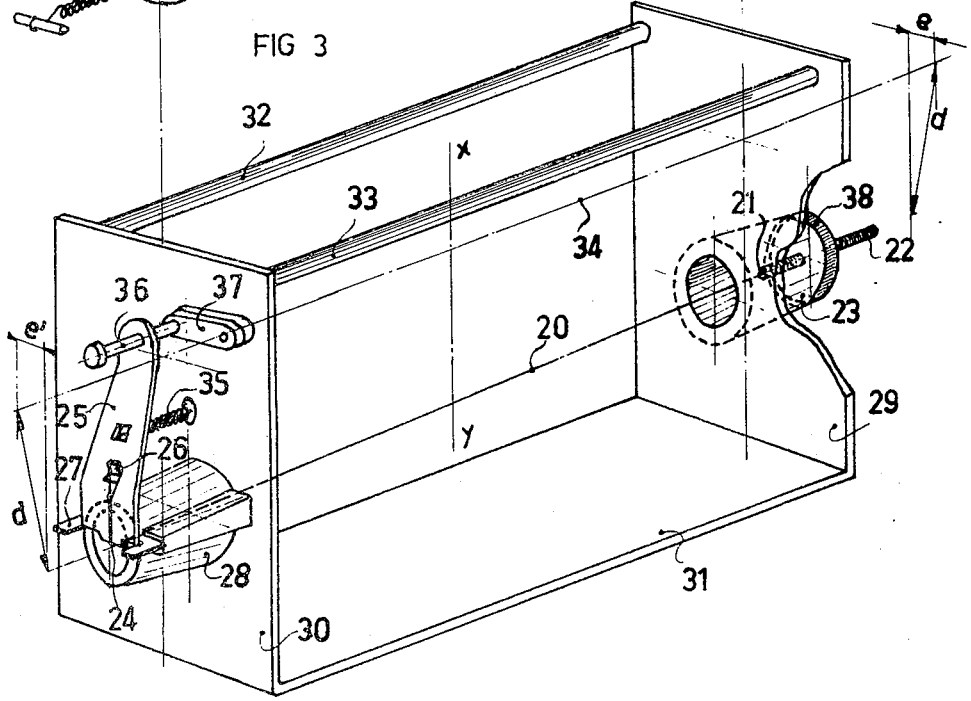
FIG. 3 is a perspective view of one exemplary embodiment of a device for thermostatic regulation and for removing cooked pancakes.

FIG. 3 shows the machine frame without the cooking cylinder. The reference 20 denotes the device for thermostatic regulation and for removing cooked pancakes in the form of a rigid stainless steel wire stretched between anchoring point 21 and the end of an adjusting screw 22 in the axis of a vent 23, and the supporting point 24 at the end of a lever 25 formed with a stud 26 which is used for securing the end of said thermostatic wire. The lever 25 rests against a blade 27 which is itself accommodated in a second vent 28. The wire 20 can be placed under permanent tension by means of a spring 35 acting on the lever 25.

The two slightly frustoconical vents 23 and 28 with horizontal axes are an integral part of the two end plates 29 and 30. The machine frame, comprising these two end plates, the base plate 31 and the upper crossbars 32 and 33 forms a non-deformable assembly. The cooking cylinder (reference 10 in FIG. 2) is normally mounted between the end plates 29 and 30 and rotates about an axis denoted by the reference 34 in FIG. 3.

The fastening points 21 and 24 of the wire 20 are situated at the same distance $d$ from the axis 34, which is less than the radius R of the cooking cylinder, but in vertical projection in the horizontal plane containing the axis 34, these two fastening points are situated on either side of said axis at intervals $e$ and $e'$ equal to or slightly different from one another. As explained in reference to FIG. 1, each point of the wire 20, which is rectilinear in the absence of the cooking cylinder, is at a distance from the axis 34 which decreases from the point 24 to the vertical axis of symmetry XY and subsequently increases again up to the point 21. When the cooking cylinder is introduced into the frame on its axis 34, the wire 20 assumes the appearance represented by the line 11–13 in FIG. 2, i.e. a spiral arc with a wide helix angle. As has also been pointed out, this wire applies pressure over the entire length of the surface of the cylinder, the contact pressure forces being greater, the closer the points of the wire come to the axis of symmetry XY. The stripping effect of the stretched wire, which is produced when it is directed along a generatrix, is thus eliminated and, when the cooking cylinder rotates, the cooked pancakes are removed in perfect order.

In addition, this uniform adherence of the wire 20 over the entire cooking surface enables this wire closely to follow variations on the temperature of the cylinder over the cooking surface. Thus, as pointed out earlier on, it gives a true image of the real temperature of the cylinder. It expands under the effect of the heat transmitted by conduction, and the variations in temperature are reflected in variations in the length of said wire. As these variations in length are obviously limited, the lever 25 enables them to be amplified, this lever oscillating about the edge of the blade 27 at such a point that the ratio of amplification of the arms is, for example, from 1 to 15. The upper end of the lever 25 is provided with a micrometric adjusting screw 36 which acts on a microswitch 37 installed in the electrical feed circuit of the heating resistances incorporated in the cooking cylinder.

The device for thermostatic regulation and for removing cooked pancakes is positioned and adjusted as follows:

The wire 20 is formed into a closed loop at each of its ends, being introduced into the vent 23 and fastened to the end of the screw 22 which is pre-equipped with a support washer 38 and an adjusting nut (not shown).

The other end of the wire 20 is then introduced into vent 28 from inside the frame and the end loop is fastened to the stud 26. The lever 25 is held in its definitive position by engaging the spring 35.

Assembly of the machine is then completed, in particular with the cooking cylinder and the heating device, followed by rough adjustment by means of the screw 22, the tolerance of the length of wire between loops being extremely wide. The wire is then placed under tension and under the control of a pyrometer. The release point of the microswitch 37 is regulated by acting manually on the micrometric screw 36.

The stripping wire 20 should have a high resistance to wear by friction and a relatively high coefficient of linear expansion. Various metals are suitable for this purpose, so-called "piano chord" steel wire being particularly suitable.

Nevertheless, the arrangement described above in reference to FIGS. 1, 2 and 3 is attended by certain disadvantages arising out of the simplified mounting of its components. In particular, the amplifying power of the lever 25 is too great for commercial microswitches 27. As a result, the movement of the end of the lever stops when the screw 36 comes into contact with the moving armature of the microswitch, the actuating force being incompatible with the force applied by the spring 35. If the force of the spring 35 is increased, the resulting tractive force on the stripper wire becomes excessive before the microswitch is operated.

In addition, difficulties are involved in arranging the blade 27, the lever 25, the spring 35 and the microswitch 37 in a chain, apart from which reliability is poor.

Figure 4:
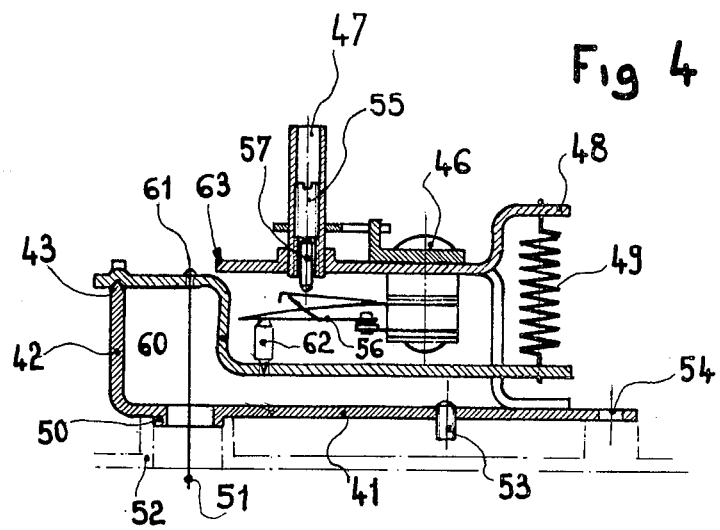
FIG. 4 is a longitudinal section through a subassembly which will be referred to hereinafter as a "make-and-break slack adjuster"
Figure 5:
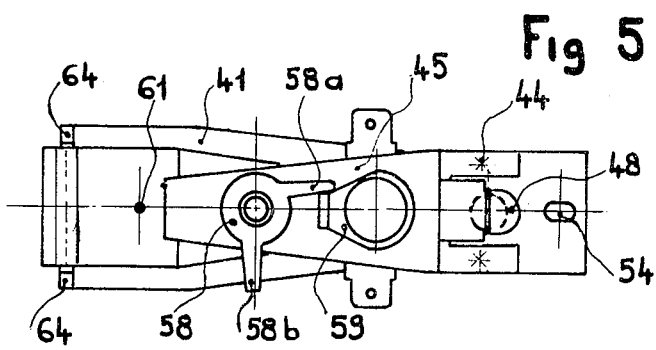
FIG. 5 is a view of the sub-assembly from above.
Figure 6:
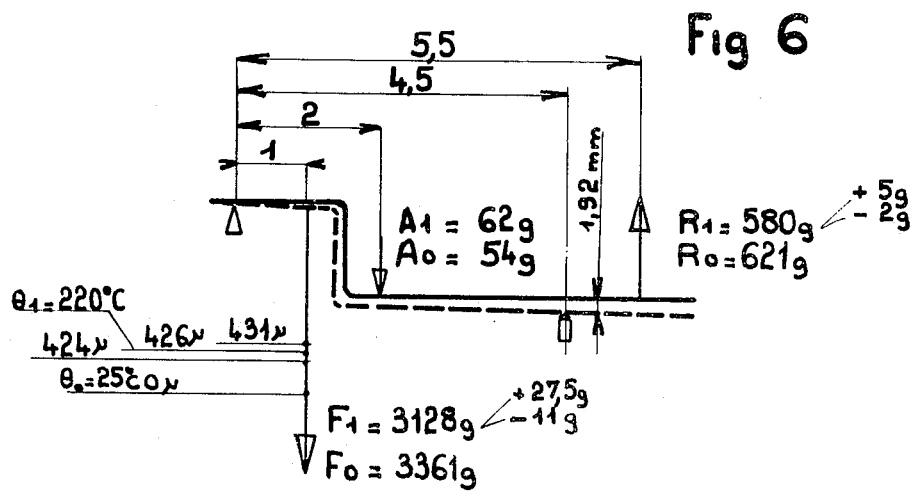
FIG. 6 is the diagrammatic view of the regulating device.

These technical deficiencies can be obviated. To this end, the components 27, 25, 35 and 37 as a whole can be regrouped into a separate sub-assembly, pre-assembled and pre-regulated in an adjacent chain, so that it is easy to instal in the machine and to replace in the event of failure. Reference is made to FIGS. 4 to 6.

The essential elements already mentioned are retained in their respective functions. The main characteristic is embodied in the fact that they are assembled on a rigid base plate with means for positioning them with precision on and fixing them to the machine. The base plate is equipped with two other new components, namely:

a. an adjusting screw which enables the make-and-break slack adjuster to be pre-regulated to the operating temperature of the machine; and b. a screw for adjusting the force required for actuating the moving armature of the microswitch. This particular screw enables the working temperature of the machine to be varied within a certain range as required by the user.

A second feature is embodied in the fact that the lever forming part of the make-and-break slack adjuster is integral with the base plate and cannot be separated from it either during transport or during handling.

On the operating level, the balance of forces acting on the lever when the make-and-break slack adjuster is mounted on the machine is different from that previously described, because the moving armature of the microswitch is permanently under the influence of the lever and, as a result, no longer shows a sudden increase in the force to be applied by said lever. In order to minimize this force, the amplification ratio is in the range from 2–3 to 1. In addition, the spring by which the wire is kept under tension is mounted at the end of the lever with a high ratio (for example 5–6 to 1).

The base plate 41, made of curved, cut sheet steel, comprises on one side a right-angled bend 42 which at its end forms a knife edge 43. On its other side, assembled by electrical spot welding 44, the base plate at its upper end is in the form of a support 45 receiving the constituent elements of the contact breaker assembled by riveting 46, and an adjusting screw 47. The tension spring 49 is anchored to a tab 48.

In addition, the base plate comprises an opening 50 for allowing the stripper wire 51 through and for automatically centring the sub-assembly in the end plate of the machine 52. A screw 53 provides for pre-regulation according to circumstances, as will be described hereinafter. Finally, a hole 54 provides for fixing to the end plate of the machine by means of screws.

The screw 47 has an axial tapped hole receiving a screw 55 for regulating the breaking force. Action on the moving armature 56 of the contact breaker is by a "rice grain" insulator 57. A double-stop ring 58 is welded to the screw 47. These stops limit the rotation of the screw by means of the stud 59.

The constituents of the contact breaker are those of a thermostat and, for this reason, do not give rise to any difficulties in terms of design and fitting.

The lever 60 bears on the cutting edge 43 and receives the end of the stripper wire 51 through a hole 61. The moving armature of the contact breaker is actuated by a rice grain insulator 62 arranged inbetween. The stripper wire 51 is placed under tension by the spring 49 at the end of the lever. Said end of the lever traverses the vertical part of the base plate through an opening formed during cutting out of the tab 48.

It should be noted that the end 63 of the upper part of the base plate is in direct contact with the bend in the lever, which prevents the lever from being deflected upwards when the sub-assembly is not mounted on a machine. On the other hand, the parts 64 adjacent the cutting edge prevent any lateral displacement of the lever.

FIG. 6 shows the static equilibrium of the system in the two extreme cases.

Index 0 - in broken lines - position at ambient temperature.
Index 1 - in a solid line - position at the operating temperature.

In a prototype test, the parameters were as follows:

| ambient temperature | $\theta_0 = 25°C$ |
| operating temperature | $\theta_1 = 220°C$ | the stripper wire expands by 426 $\mu$ which, taking into account the amplifications indicated in the plan, gives
variations in the force of the tension spring from 621 g to 580 g ($\Delta R = 41$ g),
variations in the force of the moving armature from 54 g to 62 g ($\Delta A = 8$ g),
and variations in the tension of the stripper wire from 3.361 g to 3.128 g ($\Delta f = 233$ g).

This variation in tension gives rise to two derivative phenomena:
1 - a variation in the length of the wire through its own elasticity,
2 - a variation in the position of the anchoring points of the wire due to the elasticity of the side plates of the machine (points 21 and 24 in FIG. 3).

However, these derivative elasticities are not significant in the regulating zone, as will be demonstrated hereinafter.

When the wire has expanded by 426 $\mu$, the armature 56 moves away from its dead point and opens the contacts, the force applied by the armature changes from 62 g to a lower value (not measured) which produces an increase in the length of the stripper wire by a few microns. This increase in length is then increased by the thermal inertia of the heating means of the heating cylinder. Elongation stabilises at 431 $\mu$ ($\Delta + 5°C$). Cooling of the cylinder then begins and, when the wire has again reached a length of 426 $\mu$, the moving armature passes its dead point in the other direction and closes the contacts. The phenomenon of variation in force and thermal inertia recurs, but in the opposite direction, so that the wire contracts to 424 $\mu$ (i.e. $\Delta = 2 \mu$).

For a variation in length of the stripper wire of 7 $\mu$, the temperature variations measured on the heating cylinder are on average 5°C.

In addition, the variations in length of the tension spring produce differences in force of 7 g which are reflected in the stripper wire by variations in traction of 38.5 g. These values produce hardly any change in the length of the wire of anchoring points, which is verified by a temperature difference of only 5°C.

The device described above is regulated as follows:
When the constituents of the contact breaker are assembled the adjusting screw 47 is positioned in such a way that the stop 58a is in contact with the stud 59.

With the rice grain insulator 62 not yet engaged between the lever and the moving armature, a vertical upward force is applied by any suitable means to the armature at the point of contact of the rice grain insulator. The screw 55 is then screwed until the armature 56 moves away from its dead point.

The rice grain insulator 62 is then put in position. A 1.92 mm thick (or experimentally determined value) wedge is then placed between the lever and the adjusting screw 53. The thickness of this wedge corresponds to the displacement of the lever opposite the screw 53 from ambient temperature to operating temperature.

The lever is weighted at the point 61 so as to keep the wedge in position, i.e. somewhat more than 3.361 g, and the screw 53 is regulated until the armature 56 moves away from its dead point.

Thus, when the make-and-break slack adjuster is installed in a machine, it is sufficient to stretch the stripper wire by turning the nurled wheel 38 (FIG. 3) until the lever is brought into contact with the screw 53. Once the operating temperature has been reached, cutout will take place without further adjustment. Adjustment can still be complete with precision by turning the nurled wheel 38. In order to modify the working temperature, the user will have the possibility of manipulating the screw 47 (by suitable means) in an angular sector 58a – 58b. The effect of such handling will be to vary the position of the dead point of the armature 56, which is comparable with a variation in the length of the stripper wire.

In the application of the invention to automatic machines for making pancakes, as described in the foregoing, it has been assumed that the necessary heat has been supplied by electricity. However, it is also possible to use gas-heating or steam-heating systems, in which case the microswitch wll be incorporated in the feed circuit of an electrovalve.

Thermostatic regulation by the stripper wire can be used on its own and, in this case, it can also be used for regulating a cooling system, such as the refrigeration circuit of a calander roll.

The use of a wire stretched by a spring so that it is pressed along a helical path onto a cooking cylinder solely for the purpose of removing pancakes or other cooked products is also within the scope of the invention.

I claim:

1. In a cooking appliance of the kind including a heating cylinder bearing a cooking surface the temperature of which is controlled by a thermostatic regulating device, the improvement that the thermostatic regulating device comprises a metal wire applied under longitudinal tension along a spiral path with a large helix angle to the surface of the aforementioned cylinder, one end of the wire being fixed to a regulating screw and its other end to the short arm of an amplification lever whose long arm is acted upon by the spring, each end of the wire being situated on the axis of a vent fixed to a side plate, a first vent being used to support the adjusting screw, whilst the second vent accommodates a blade about which the lever oscillates, the heating cylinder being mounted on an axis of rotation between the two side plates, and the end of the long arm of the lever acts on a microswitch through a micrometer adjusting screw.

2. A regulating device as claimed in claim 1, wherein the end of the long arm of the lever is applicable directly to a microswitch, the interval at ambient temperature between said end and the microswitch being regulated on the production line by means of the adjusting screw and a spacer wedge whose thickness is experimentally determined.

3. A regulating device as claimed in claim 2, wherein the microswitch is mounted on a flexible base plate which is fixed to the corresponding guide plate and which enables adjustments to be made during operation through deformation effected by means of a knurled adjustment device.

4. A regulating device as claimed in claim 1, wherein the microswitch is incorporated in the feed circuit of the electrical heating resistances.

5. A regulating device as claimed in claim 1, wherein the cylinder is fluid-heated, and the microswitch is incorporated in the control circuit of an electrovalve controlling the supply of fluid.

6. In a cooking apparatus comprising a heating circuit associated with a heating cylinder, the cylinder having a thermostatically regulated cooking surface thereon, the improvement comprising:
 a. a thermostatic regulating device comprising a metal wire positioned on and extending along said cylinder in the form of a partial helical path having a large helix angle with resect to said cylinder, said wire further being under longitudinal tension;
 b. a switch in the heating circuit for said cylinder; and
 c. means for operating said switch in response to variations in length of said metal wire, said variations resulting from expansion or contraction of said wire as a result of temperature changes therein.

7. A thermostatic regulating device as recited in claim 6 including means for amplifying said variations prior to application to said switch.

8. A thermostatic regulating device as recited in claim 7, further comprising a spring for tensioning said metal wire, whereby said wire applies to said cylinder a substantially constant force at all points of contact therewith.

9. A thermostatic device as recited in claim 8, including a regulating screw attached to one end of said metal wire, wherein:
 a. said amplifying means comprises a lever having a long arm and a short arm;
 b. said wire being fixed to said short arm, and
 c. said spring being connected to said long arm of said amplification lever.

10. A thermostatic regulating device as recited in claim 9, further comprising:
 a. a blade acting as a fulcrum for said amplification lever;
 b. a first vent, having a first axis, for supporting said adjusting screw;
 c. a second vent, having a second axis, for accommodating said blade;
 d. A first side plate fixed to said first vent;
 e. A second side plate fixed to said second vent, wherein:
 f. a first end of said wire is situated on said first axis of said first vent;
 g. a second end of said wire is situated on said second axis of said second vent; and
 h. said heating cylinder is mounted on an axis of rotation between said two side plates.

11. A thermostatic regulating device as recited in claim 10, further comprising a micrometer adjusting screw, wherein an end of said long arm of said lever acts on said switch through said micrometer adjusting screw.

12. A thermostatic regulating device as recited in claim 7 wherein said metal wire is made of steel.

13. A thermostatic regulating device as recited in claim 7, wherein said cylinder cooks pancakes in contact therewith, and said metal wire removes said pancakes from said cylinder.

14. A heat-regulating sub-assembly for a heating surface with a heating circuit connected thereto and having a metal wire applied thereon, said wire being under longitudinal tension and expanding and contracting in response to temperature variation, said expansion and contraction of said wire being amplified and acting upon a contact breaker incorporated in the heating circuit of said cylinder, wherein:
 a first means for placing said metal wire under tension, a second means for breaking said heating circuit and a third means for amplification of expansion and contraction of said wire are permanently assembled on a rigid base place having means for centering and fixing said first, second and third means to a frame of a machine incorporating said heating surface.

15. A heat-regulating sub-assembly as recited in claim 14 further comprising an adjusting screw on said base plate for adjusting the position of said amplification means at ambient temperature.

16. A heat-regulating sub-assembly as recited in claim 15, wherein a moving armature of said circuit breaking means is permanently in contact with said amplification means, and applies to said amplification means an elastic force at all positions of said amplification means.

17. A heat-regulating sub-assembly as recited in claim 14, wherein an adjusting screw on said base plate is positioned for enabling a variation in the force required to move a moving armature of said circuit breaking means from a dead point of said armature.

18. A heat-regulating sub-assembly as recited in claim 14, wherein an adjusting screw on said base plate is positioned for enabling modification of the position in which a moving armature of said circuit breaking means passes its dead point.

* * * * *